United States Patent
Weng et al.

(10) Patent No.: US 9,176,040 B2
(45) Date of Patent: *Nov. 3, 2015

(54) APPARATUS AND METHOD FOR MEASURING FLUID VISCOSITY

(75) Inventors: Huei Chu Weng, Zhongli (TW); Yuan Kai Kao, Yongkang (TW)

(73) Assignee: Chung Yuan Christian University, Chung Li (TW)

( * ) Notice: Subject to any disclaimer, the term of this patent is extended or adjusted under 35 U.S.C. 154(b) by 524 days.

This patent is subject to a terminal disclaimer.

(21) Appl. No.: 13/190,659

(22) Filed: Jul. 26, 2011

(65) Prior Publication Data

US 2012/0022806 A1 Jan. 26, 2012

(30) Foreign Application Priority Data

Jul. 26, 2010 (TW) .............................. 099124598 A

(51) Int. Cl.
*G01F 17/00* (2006.01)
*G01N 11/06* (2006.01)

(52) U.S. Cl.
CPC ...................................... *G01N 11/06* (2013.01)

(58) Field of Classification Search
CPC ..................................................... G01N 11/06
USPC .................. 702/50, 45, 55, 138, 140, 47–48; 73/54.01, 53.01, 54.04, 54.11, 54.13
See application file for complete search history.

(56) References Cited

U.S. PATENT DOCUMENTS

| | | | | |
|---|---|---|---|---|
| 5,272,912 A * | 12/1993 | Katsuzaki | ...................... | 73/54.08 |
| 8,155,896 B2 * | 4/2012 | Wargo et al. | ...................... | 702/50 |
| 2003/0010096 A1 * | 1/2003 | Long | ............................ | 73/54.09 |
| 2006/0180537 A1 * | 8/2006 | Loftis et al. | .................... | 210/209 |
| 2007/0023644 A1 * | 2/2007 | Gard et al. | ...................... | 250/288 |
| 2011/0126614 A1 * | 6/2011 | Belitsch | ........................ | 73/54.04 |
| 2011/0239744 A1 * | 10/2011 | Auradou et al. | ............. | 73/54.04 |
| 2012/0084024 A1 * | 4/2012 | Norcross, Jr. | ................... | 702/50 |

OTHER PUBLICATIONS

P D Davis, G D Parabrook, G N C Kenny, "Basic Physics and Measurement in anaesthesia", 1995, Butterworth Heinemann, fourth edition, pp. 1-25, 38-40, 141, and 338.*
Henrik Bruus, "Theoretical microfluidics", Fall 2006, DTU, Lecture note third edition, 12-15, 27 and 47.*
P D Davis and G N C Kenny;"Basic Physics and Measurement in Anaesthesia"; 2003; fifth edition; 5-20, 120-124.*

* cited by examiner

*Primary Examiner* — Michael Nghiem
*Assistant Examiner* — Eman Alkafawi
(74) *Attorney, Agent, or Firm* — Rosenberg, Klein & Lee

(57) ABSTRACT

An apparatus and a method for measuring fluid viscosity are revealed. An inlet end of a container is larger than an outlet end of the container. A fluid flows through the outlet end at a flow rate. A volume of the fluid flowing out of the outlet end is measured by a graduated cylinder while the time taken for the fluid to flow through the outlet end is measured by a timer. The flow rate is associated with the volume and the time of the fluid and the viscosity of the fluid is obtained according to a density and a pressure gradient of the fluid, an outlet end radius and the flow rate. The apparatus has simple structure, easy operation and maintenance. Moreover, less space is required and the apparatus cost is low. Therefore, the testability is improved, the measurement time is reduced, and the convenience in use is enhanced.

10 Claims, 9 Drawing Sheets

APPARATUS AND METHOD FOR MEASURING FLUID VISCOSITY

BACKGROUND OF THE INVENTION

1. Fields of the Invention

The present invention relates to a measuring apparatus and a measuring method, especially to an apparatus and a method for measuring fluid viscosity.

2. Descriptions of Related Art

Viscosity is one of the important physical properties and is a measure of the resistance of a fluid. The more viscous the fluid is, the lesser its ease of movement. In our daily lives, there are phenomena related to the viscosity such as the taste of drinks, the degree of difficulty in painting, the writing fluency of a fountain pen. Among industrial technologies, there are also a lot of applications related to the viscosity such as a damping device, dip-feed lubrication, fuel oil transfer, and fuel oil atomization etc. The most common viscometers that measures fluid viscosity are rotary viscometers, glass capillary viscometers, and falling ball viscometer.

A rotary viscometer, as revealed in U.S. Pat. No. 5,287,732, and No. 6,240,770, includes an outer cylinder, an inner coaxial cylinder, and a test liquid in a measuring gap formed between the outer cylinder and the inner cylinder. By rotating the inner cylinder, tangential velocity of the fluid at the wall is changed. Both the torque obtained and the tangential velocity are substituted into Newton's stress-strain equation so as to get the viscosity of the test liquid. The rotary viscometer has advantages of short measurement time, and simple instrument operation. However, the gap between the outer cylinder and the inner cylinder is quite small. Once the fluid contains granules therein such as slurry or suspension, the rotary viscometer doesn't work and its testability is reduced. Moreover, the length of each cylinder is quite long for reducing measurement error. Thus the viscometer occupies space and costs a lot. Furthermore, the length of two cylinders, the gap, location, the shape of the bottom of the cylinder, friction, and residual liquid all have effects on the measurement precision and cause increased measurement error. While measuring viscosity of different fluids, the viscometer needs to be disassembled and cleaned so as to prevent unexpected errors caused by residual fluid. Therefore the management and maintenance of the rotary viscometer are more difficult.

As to the glass capillary viscometer, it includes a U-shaped glass tube with a test liquid therein and two glass bulbs, also known as Ostwald viscometer. One arm of the U-shaped tube is a capillary and the other arm is a normal tube respectively connected to a glass bulb. One glass bulb is lower down than the other one. Due to gravity, the liquid flows in the capillary. The flow rate of the liquid in the capillary is obtained indirectly by control of the level of the liquid in two glass bulbs. By substituting the known flow rate into an equation for viscosity versus flow rate, the viscosity of the test liquid is obtained. Compared with rotary viscometer, the advantage of the glass capillary viscometer is with higher testability, less space and lower cost. However, in order to reduce measurement error, the two glass bulbs should be with larger volume. Moreover, up and down movements of the fluid level take a long time so that the measurement time is extended. Furthermore, the movements of the liquid level in the two glass bulbs cause hydrostatic pressure changes at the outlet end and this influence the measurement precision and further the measurement error is increased. In addition, the capillary diameter is quite small and difficult to be cleaned properly. Thus the maintenance is getting difficult. The liquid level moves freely in the two glass bulbs so that the operation for control of level movement is quite complicated. Besides, once the liquid has high viscosity or granules whose diameter is closed to the capillary diameter, the glass capillary viscometer is not suitable. The testability of the glass capillary viscometer is not high. In order to reduce measurement errors, the volume of each glass bulb is quite large so that the space required is increased. And the capillary is an integrated tube produced with high technical cost. Thus the high cost is still an issue.

Refer to Taiwanese Pat. Pub. No. 200912277, a conventional falling ball viscometer consists of a vertical tube and a ball. A test liquid is in the vertical tube. The ball is allowed to descend through the liquid in the vertical tube due to gravity. A velocity of the falling ball is learned and is substituted into an equation for viscosity versus velocity. Compared with the glass capillary viscometer, its advantages are short measurement time, low instrument cost, and easy operation. However, it's difficult to observe and measure if the test liquid is not clean and transparent. The testability is still not improved. Moreover, the ball size compared with the vertical tube, the surface deterioration and abrasion all have affects on the measurement precision. Thus the measurement error is large. The ball is a consumable and this causes difficulties in maintenance.

In order to overcome above disadvantages, there is a need to provide an apparatus and a method for measuring viscosity that not only improves testability but also reduces measurement time, space required, instrument cost, measurement error, difficulty in maintenance and operation complexity for solving the problems.

SUMMARY OF THE INVENTION

Therefore it is a primary object of the present invention to provide an apparatus and a method for measuring fluid viscosity. By a container in which an inlet end is larger than an outlet end, an equation is derived based on a fact that a viscosity value of the fluid is correlated with a flow rate value and a pressure gradient value. The flow rate is measured by a graduated cylinder and a timer. Then the viscosity is obtained according to the flow rate. Thus the testability is improved and the measurement time is reduced. Moreover, the present invention has simple structure so that maintenance and operation are quite easy. Not only the space required is less, the apparatus cost is low and the measurement error is reduced.

It is another object of the present invention to provide an apparatus and a method for measuring fluid viscosity in which a pressure controller for control of the pressure gradient of the fluid is connected to the inlet end and the outlet end so as to get more precise pressure gradient of the fluid and further obtain more precise viscosity of the fluid.

It is a further object of the present invention to provide an apparatus and a method for measuring fluid viscosity in which a weight measuring device measures weight of the fluid flowing out of the container and a timer measures a time required for the fluid to pass the outlet end. A more precise flow rate is obtained according to the weight, the time and a density of the fluid. A more precise viscosity of the fluid is further got.

It is a further object of the present invention to provide an apparatus and a method for measuring fluid viscosity in which a microprocessor calculates a viscosity value according to the density, the pressure gradient, a radius of the outlet end and the flow rate. The convenience in use of the present invention is further enhanced.

In order to achieve above objects, an apparatus for measuring fluid viscosity of the present invention consists of a container, a fluid, a graduated cylinder and a timer. The container is disposed with an inlet end and an outlet end while the inlet end is larger than the outlet end. The fluid with a density and a pressure gradient is within the container and flowing out of the outlet end at a flow rate. The graduated cylinder measures a volume of the fluid flowing out of the outlet end while the timer measures a time taken for the fluid to flow out of the outlet end. The flow rate is associated with the volume and the time. The viscosity of the fluid is correlated with the density, the pressure gradient, a radius of the outlet end, and the flow rate. The apparatus has a simple structure so that both maintenance and operation are easy. Moreover, less space is required, the cost is down and the measurement error is reduced, Moreover, the present invention further includes a pressure controller for control of the pressure gradient of the fluid and connected to the inlet end and the outlet end. Thus a more precise pressure gradient of the fluid is given and a more precise fluid viscosity is obtained. Moreover, the present invention further includes a weight measuring device for measuring weight of the volume of the fluid and placed under the graduated cylinder. A timer is used to measure a time required for the fluid to pass the outlet end. In accordance with the weight, the time and the density of the fluid, a more precise flow rate is obtained and a more precise viscosity of the fluid is further measured.

Furthermore, the present invention further includes a microprocessor that calculates the fluid viscosity value according to the density, the pressure gradient, a radius of the outlet end and the flow rate. This enhances the convenience in use.

The method for measuring fluid viscosity of the present invention includes following steps. Firstly, measure a pressure gradient of a fluid in a container. The fluid flows into the container through an inlet end of the container and flows out of an outlet end of the container. Then measure a flow rate of the fluid flowing out of the outlet end. Finally, get a viscosity of the fluid according to a density, the pressure gradient, a radius of the outlet end, and the flow rate at the outlet end. The present invention can be applied to different fluids. Thus the testability is improved, the measurement time is reduced and the convenience in use is enhanced,

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
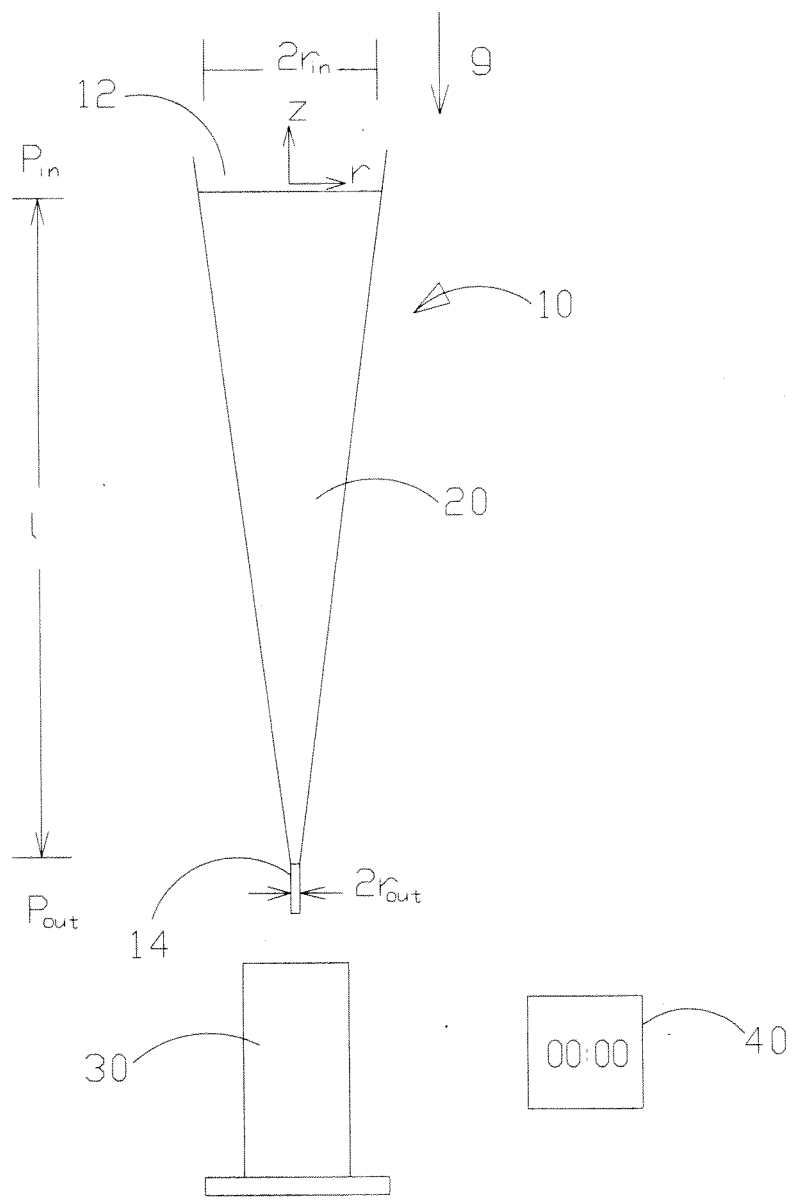
FIG. 1 is a schematic drawing showing structure of an embodiment of an apparatus for measuring fluid viscosity according to the present invention.

Refer to FIG. 1, an apparatus for measuring fluid viscosity of the present invention includes a container 10, a fluid 20, a graduated cylinder 30 and a timer 40. The container 10 is disposed with an inlet end 12 and an outlet end 14 while the inlet end 12 is larger than the outlet end 14. The fluid 20 is stored in the container 10. The container 10 of the present invention is a reducer in which the fluid 20 to be tested is placed. The fluid 20 is discharged through the outlet end 14 at a certain flow rate. The fluid 20 has a density value of ρ and a value of pressure gradient dp/dz. The fluid 20 at the inlet end 12 has an inlet pressure $p_{in}$ while the fluid 20 at the outlet end 14 has an outlet pressure $p_{out}$. The difference between the inlet pressure $p_{in}$ and the outlet pressure $p_{out}$ divided by a height l of the container 10 is the value of pressure gradient dp/dz.

Due to gravity and inlet pressure difference between the inlet end and the outlet end, the fluid 20 jets freely from the outlet end 14 while the fluid 20 around the inlet end 12 moves downward slowly. The length of the reducer 10 is larger than the diameter of the inlet and outlet ends 12, 14 so that flow field is represented as the following simplified conservation equation according to mass and momentum balance equations:

$$\left. \begin{array}{l} \dfrac{1}{r}\dfrac{\partial}{\partial r}(ru_r) + \dfrac{\partial u_z}{\partial z} = 0, \\ \dfrac{dp}{dz} = \mu \dfrac{1}{r}\dfrac{\partial}{\partial r}\left(r\dfrac{\partial u_z}{\partial r}\right) - \rho g. \end{array} \right\} \quad (1)$$

wherein r and z are two coordinates in a cylindrical coordinate system, $u_r$ and $u_z$ respectively are velocity components of r and z, p is pressure, g is acceleration of gravity, ρ is the density value of the fluid 20, µ is viscosity of a test fluid, dp/dz is the value of pressure gradient. The momentum conservation equation is integrated twice to obtain the relationship between viscosity and flow rate under the conditions of no sliding ($u_z$=0) and symmetry boundary ($\partial u_z/\partial r$=0):

$$\mu = \dfrac{\rho g + dp/dz}{4u_z(r,z)}\left(r^2 - \left(r_{out} + \dfrac{r_{in} - r_{out}}{l}(z+l)\right)^2\right) \quad (2)$$

wherein $r_{in}$ and $r_{out}$ respectively is a radius of the inlet end 12 and the outlet end 14 of the container 10, and gravity ρg and pressure gradient dp/dz are sources that drive the fluid 20. In the equation, (ρg+dp/dz)/4$u_z$ represents a driving force per unit of velocity. In the measurement, geometry of the container 10 and the mathematical statement in the brackets of the equation (2) should be considered. The flow velocity $u_z(r,z)$ at the outlet end 14 (z=−l) in the equation (2) is integrated to obtain the following equation that shows the correlation between viscosity and flow rate:

$$\mu = \frac{\pi(\rho g + dp/dz)r_{out}^4}{8\dot{Q}} \quad (3)$$

wherein $\dot{Q}$ is volume flow rate. Under the condition that the flow rate through the inlet end 12 and the flow rate through the outlet end 14 are equal to obtain the pressure gradient value:

$$\frac{dp}{dz} = 2\frac{p_{in} - p_{out}}{l} - \frac{(2(p_{in} - p_{out})/l)r_{out}^4 + \rho g(r_{out}^4 - r_{in}^4)}{r_{out}^4 + r_{in}^4} \quad (4)$$

Wherein the inlet pressure $p_{in}$ and the outlet pressure $p_{out}$, the height l of the container.

By substituting the flow rate $\dot{Q}$ of the fluid 20 at the outlet end 14, the viscosity of the test fluid 20 is obtained.

The graduated cylinder 30 measures the volume of the test fluid 20 discharged from the outlet end 14 and the timer 40 measures a time t required for a volume $V$ of the fluid 20 to be discharged. The obtained flow rate $\dot{Q} = V/t$ is substituted into the equation (3) so as to obtain the viscosity of the test fluid 20. In the present invention, the graduated cylinder 30 measures the volume $V$ of the fluid 20 drained through the outlet end 14 and the timer 40 measures the time t during which the volume $V$ of the fluid 2 flows out of the outlet end 14. The volume $V$ divided by the time t gives the flow rate $\dot{Q}$. The viscosity μ of the fluid 20 is given by substituting the density value ρ, the value of pressure gradient dp/dz, the radius $r_{out}$ and the flow rate $\dot{Q}$ into the equation (3). Thus the present invention measures the viscosity by an instrument with simple structure. Therefore the maintenance is easy and the operation is not complicated. Moreover, less space is required, instrument cost is low, and measurement error is reduced.

Figure 2A:
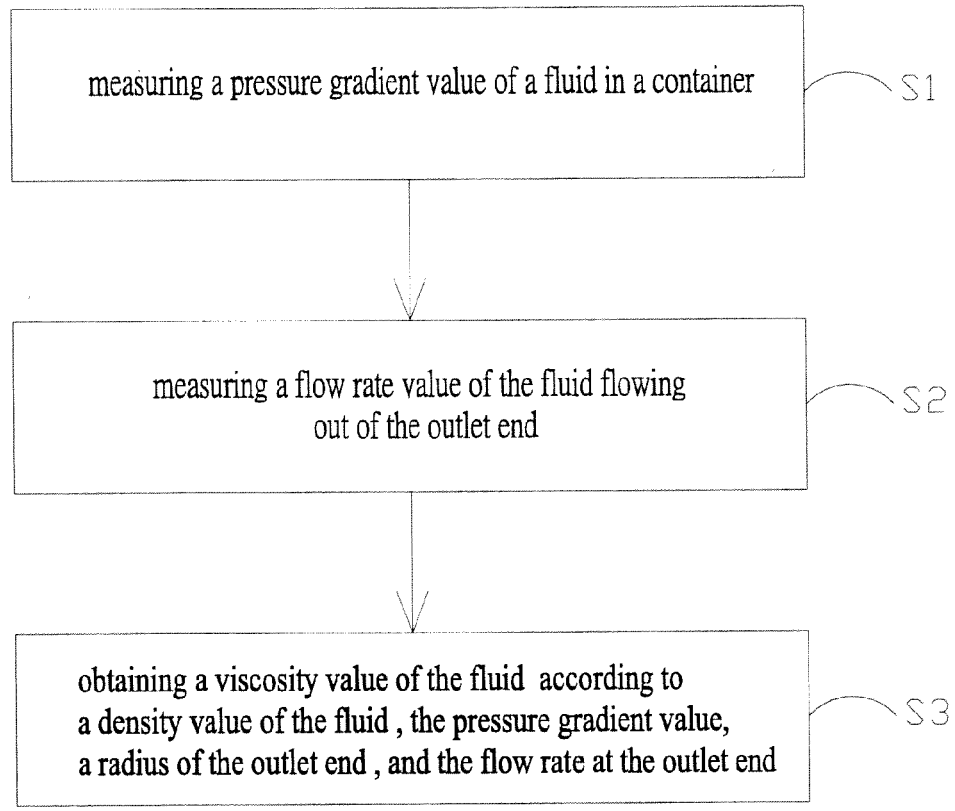
FIG. 2A is a flow chart of an embodiment of a method for measuring fluid viscosity according to the present invention.
Figure 2B:
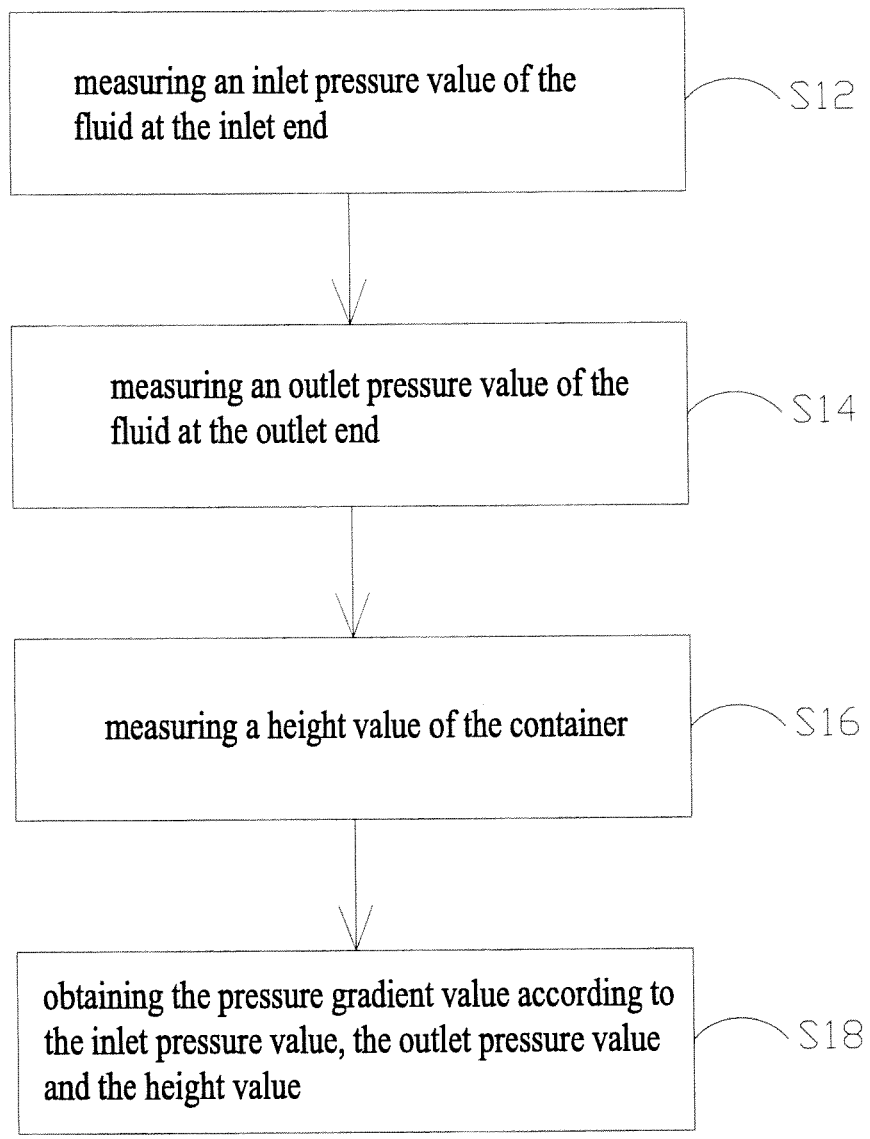
FIG. 2B is a flow chart showing how to measure pressure gradient of an embodiment according to the present invention.
Figure 2C:
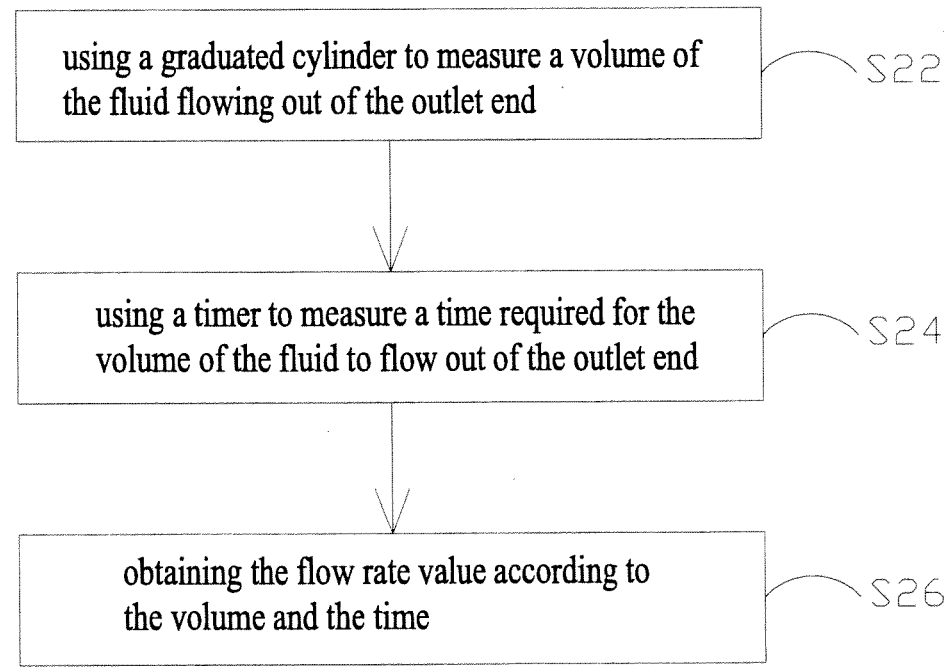
FIG. 2C is a flow chart showing how to measure flow rate at an outlet end of an embodiment according to the present invention.

Refer from FIG. 2A to FIG. 2C, a flow chart of a method for measuring fluid viscosity, a flow chart for measuring pressure gradient, and a flow chart for measuring a flow rate value at an outlet end are revealed. As shown in figure, a method for measuring fluid viscosity of the present invention includes following steps. Refer to FIG. 2A, firstly, take the step S1, measure a pressure gradient value of a fluid 20 in a container 10. Then take the step S2, measure a flow rate value of the fluid 20 flowing out of an outlet end 14. At last, run the step S3, get a viscosity value of the fluid 20 according to a density value of the fluid 20, the pressure gradient value, a radius of the outlet end 14, and the flow rate at the outlet end 14.

The step S1 consists of following steps, as shown in FIG. 2B. First of all, take the step S12, measure an inlet pressure value of the fluid 20 at an inlet end 12. Then run the step S14, measure an outlet pressure value of the fluid 20 at the outlet end 14. Next refer to the step S16, measure a height value of the container 10. Finally, take the step S18, obtain the pressure gradient value according to the inlet pressure value, the outlet pressure value and the height value.

As to the step S2, refer to FIG. 2C, it is composed of three steps. At first, take the step S22, use a graduated cylinder 30 to measure a volume of the fluid 20 discharged from the outlet end 14. Then run the step S24, use a timer 40 to measure a time required for the volume of the fluid 20 to flow out of the outlet end 14. Lastly, take the step S26, get the flow rate value according to the volume and the time.

Figure 3A:
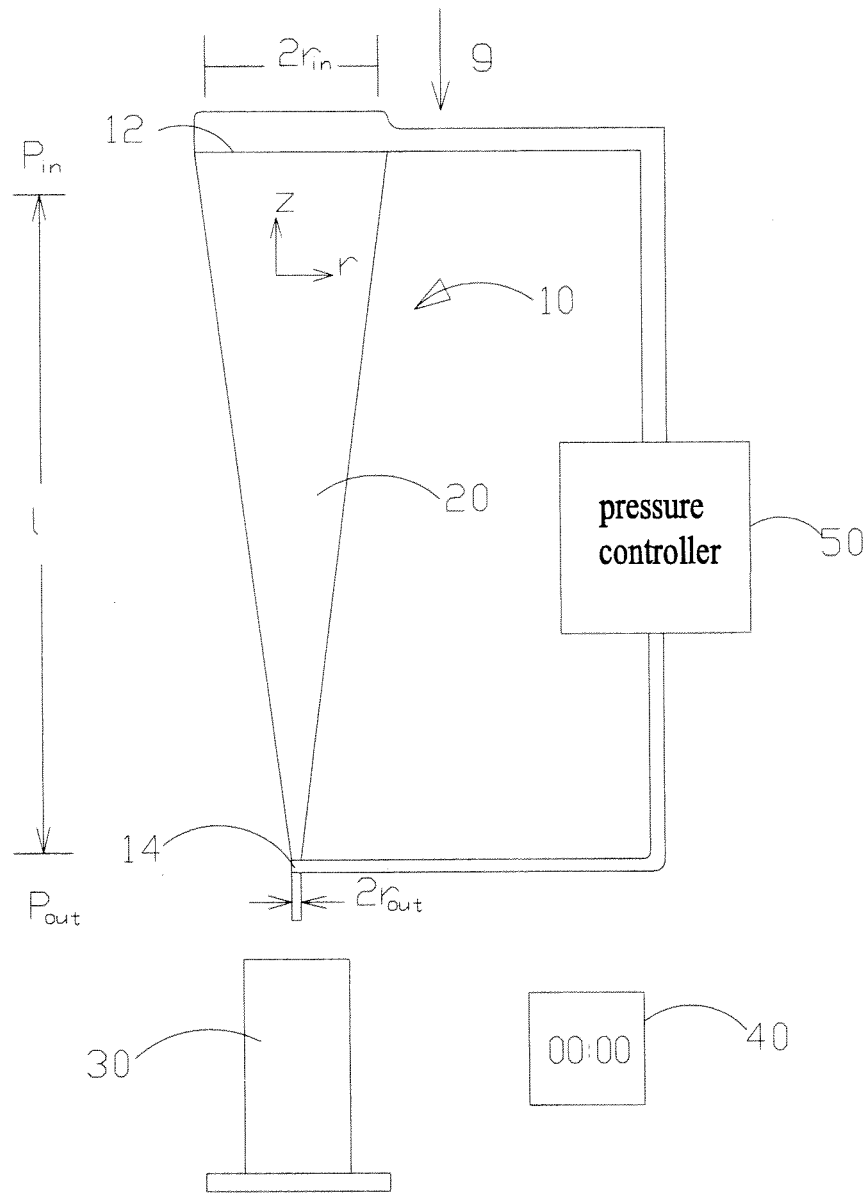
FIG. 3A is a schematic drawing showing structure of another embodiment of an apparatus for measuring fluid viscosity according to the present invention.
Figure 3B:
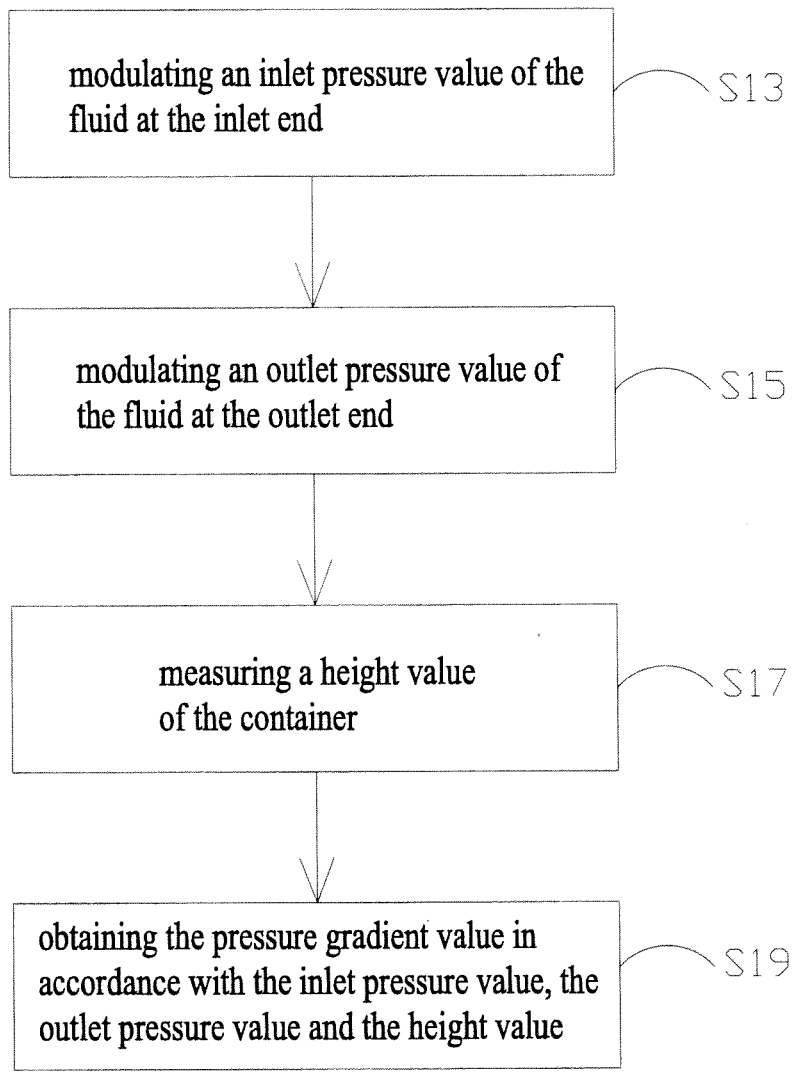
FIG. 3B is a flow chart showing how to measure pressure gradient of another embodiment according to the present invention.

Refer to FIG. 3A and FIG. 3B, a schematic drawing showing structure of another embodiment and a flow chart for measuring pressure gradient are disclosed. An apparatus for measuring fluid viscosity further includes a pressure controller 50 that is connected to an inlet end 12 and an outlet end 14 and is used for control of a pressure gradient of the fluid 20. The pressure controller 50 in this embodiment can be a pump, a piston or other devices which can control the pressure so as to control an outlet pressure $p_{out}$ and an inlet pressure $p_{in}$. Thus the pressure gradient value dp/dz is further controlled more precisely. In the step S1, the pressure gradient value dp/dz is controlled by the pressure controller 50 and the step of measuring a pressure gradient value of the fluid 20 has been changed. As shown in FIG. 3B, run the step S13 firstly, modulate an inlet pressure value of the fluid 20 at the inlet end 12. Then take the step S15, modulate an outlet pressure value of the fluid 20 at the outlet end 14. Next, run the step S17, measure a height value of the container 10. At last, take the step S19, obtain the pressure gradient value in accordance with the inlet pressure value, the outlet pressure value and the height value. Thus the pressure gradient value obtained is more accurate and the accuracy of the fluid 20 viscosity measured is improved.

Figure 4A:
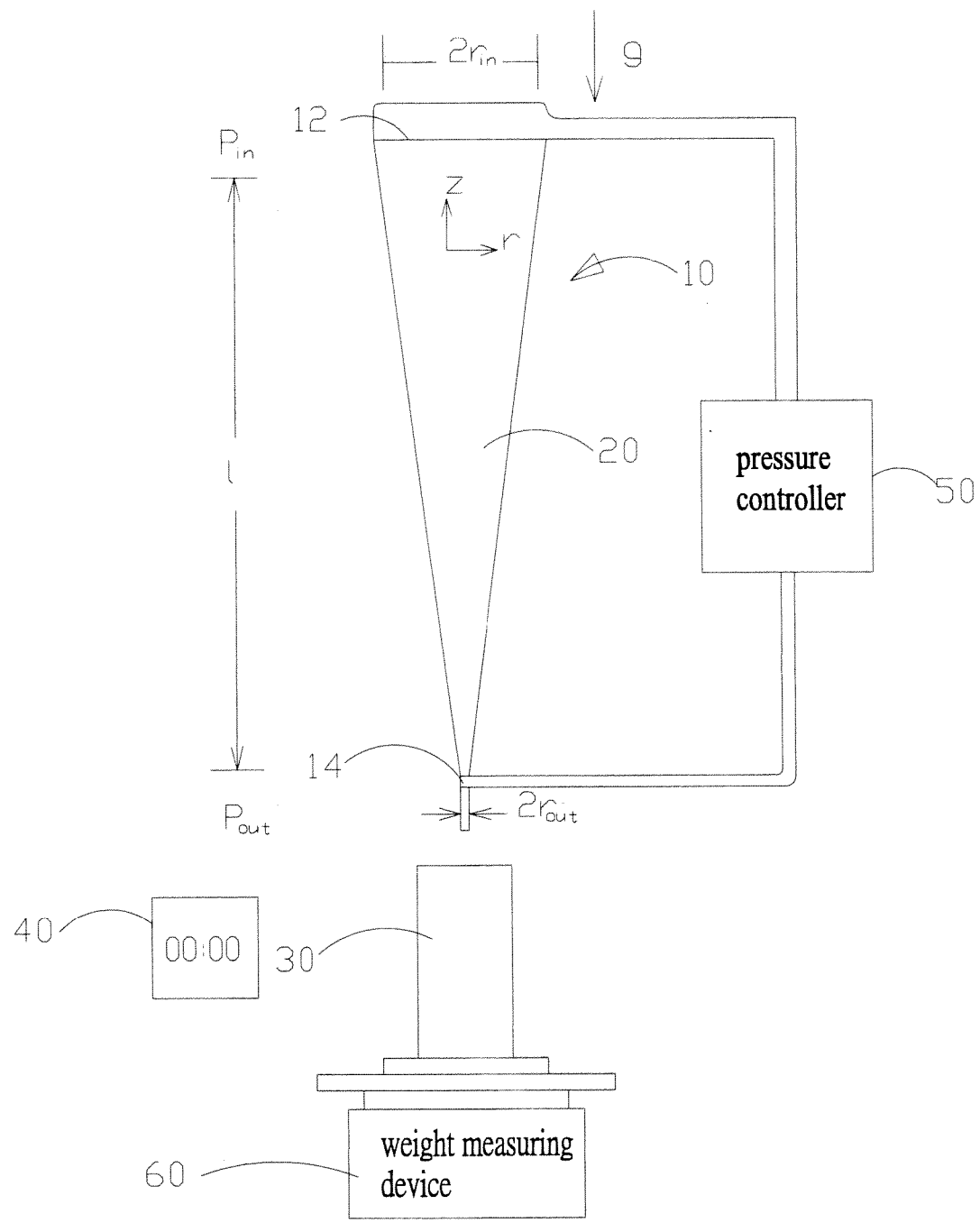
FIG. 4A is a schematic drawing showing structure of a further embodiment of an apparatus for measuring fluid viscosity according to the present invention.
Figure 4B:
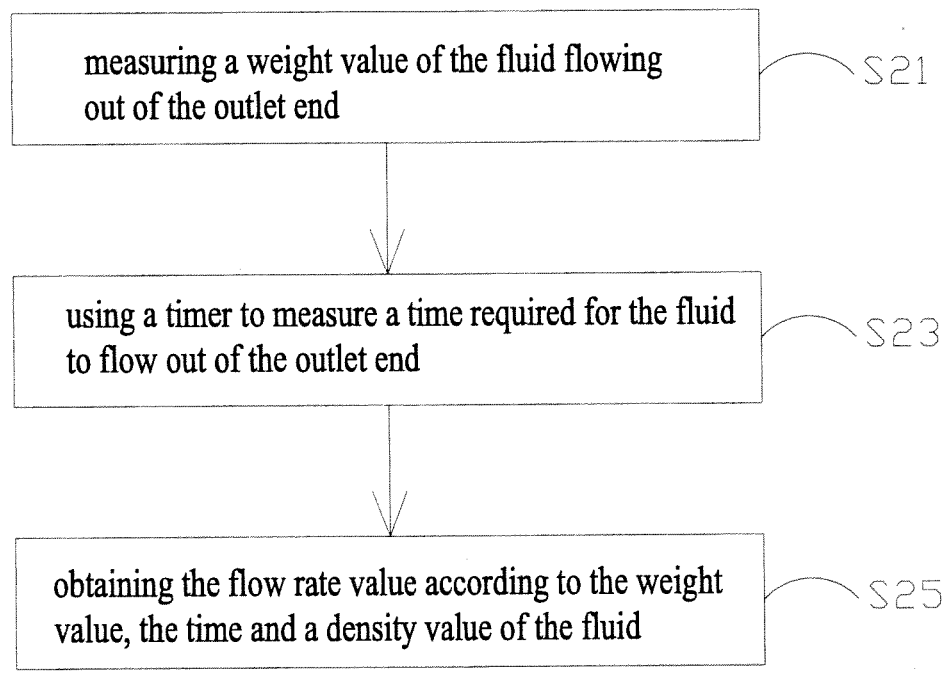
FIG. 4B is a flow chart showing how to measure flow rate at an outlet end of another embodiment according to the present invention.

Refer to FIG. 4A and FIG. 4B, a schematic drawing showing structure of a further embodiment and a flow chart for measuring flow rate at an outlet end are disclosed. As shown in figure, the difference between this embodiment and the above one is in that this embodiment further includes a weight measuring device 60 that is an electronic balance. The weight measuring device 60 is disposed under the graduated cylinder 30 for measuring weight of the fluid 20 in the graduated cylinder 30. In this embodiment, a timer 40 is used to measure a time for a volume $V$ of the fluid 20 to flow out of the outlet end 14. Moreover, the weight measuring device 60 is used to measure the weight of the fluid 20 flowing into the graduated cylinder 30. An accurate mass M of the fluid 20 flowing into the graduated cylinder is gotten by the electronic balance. Under the condition that the fluid density ρ is already known, a flow rate is obtained ($\dot{Q} = V/t = M\rho/t$). Thus a more accurate flow rate is given and the accuracy of the fluid 20 viscosity is increased.

The step S2 of measuring a flow rate value of a fluid 20 shown in FIG. 4B is different from the step S2 in FIG. 2C. Firstly, run the step S21, use a weight measuring device 60 to measure a weight value of a fluid 20 discharged from an outlet end 14. That means to measure the weight of the fluid 20 in the graduated cylinder 30. Then take the step S23, use a timer 40 to measure how long the fluid 20 takes to flow out of the outlet end 14. At last, obtain a flow rate value according to the weight value, the time and a density value of the fluid 20. Thus a more accurate flow rate value is given and the accuracy of the fluid 20 viscosity is increased.

Figure 5:
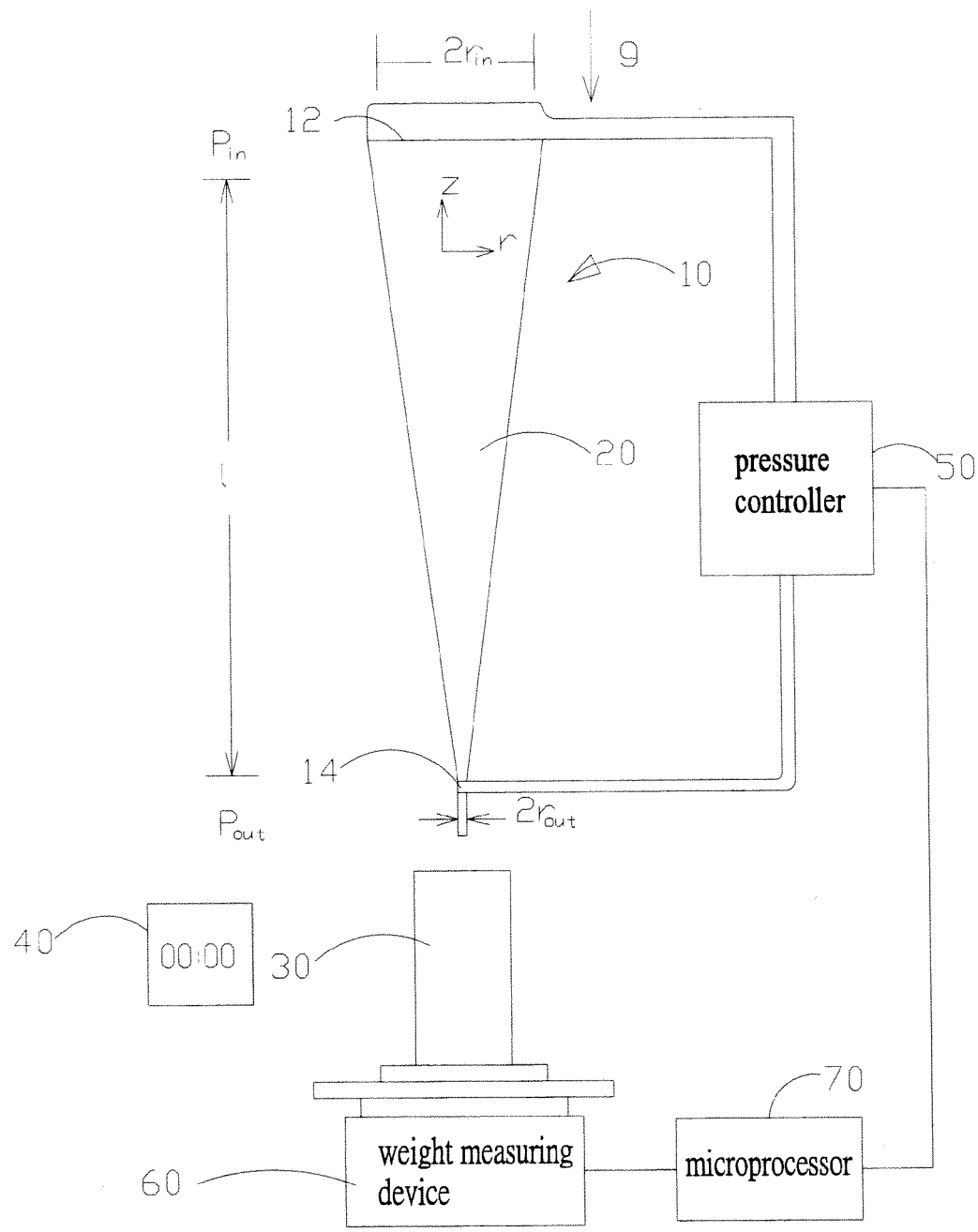
FIG. 5 is a schematic drawing showing structure of a further embodiment of an apparatus for measuring fluid viscosity according to the present invention.

Refer to FIG. 5, a schematic drawing showing structure of a further embodiment is revealed. The difference between this embodiment and the on in FIG. 4A is in that this embodiment further includes a microprocessor 70 that calculates viscosity of the test fluid 20 by substituting the density value, the pressure gradient value, the radius of the outlet end and the flow rate value into the equation (3).

In summary, the present invention provides an apparatus and a method for measuring fluid viscosity. A container is arranged with an inlet end and an outlet end while the inlet end is larger than the outlet end. A fluid stored in the container is flowing out from the outlet end at a flow rate. The fluid is with a density value and a pressure gradient value. The volume of the fluid flowing out from the outlet end is measured by a graduated cylinder and a timer is used to measure the time for the volume of the fluid to flow out of the outlet end.

The flow rate is correlated with the volume and the time. Finally, the fluid viscosity is obtained according to a density value of the fluid, the pressure gradient of the fluid, a radius of an outlet end, and the flow rate value at the outlet end. The apparatus of the present invention has a simple structure so that the maintenance of the apparatus is easy and the operation is not complicated. Moreover, less space is required, instrument cost is low, and measurement error is reduced. Furthermore, the present invention is applied to different fluids. The testability is improved and the measurement time is reduced, both enhance convenience in use.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An apparatus for measuring viscosity comprising:
a container having an inlet end and an outlet end, a radius of the inlet end is larger than a radius of the outlet end while the container is a vertical reducer, the container containing a fluid under measuring, the fluid having a density value $\rho$ and a pressure gradient value $dp/dz$, placed within the container, and flowing out of the outlet end at a flow rate value $\dot{Q}$;
a pressure controller connected to both the inlet end and the outlet end, and modulating an inlet pressure value of the fluid at the inlet end and modulating an outlet pressure value of the fluid at the outlet end to modulate the pressure gradient value $dp/dz$ of the fluid according to the inlet pressure value, the outlet pressure value and a height of the container;
a graduated cylinder, disposed under the outlet end, for measuring a volume of the fluid flowing out of the outlet end while the fluid is discharged from the outlet end; and
a timer, measuring a time during the fluid flowing out of the outlet end while the flow rate value $\dot{Q}$ is associated with the volume and the time;
a microprocessor that calculates a viscosity value $\mu$ of the fluid is defined by following Expression;

$$\mu = \pi(\rho g + dp/dz)\gamma_{out}^4/8\dot{Q} \qquad \text{Expression 1}$$

where, g is gravity, $\gamma_{out}$ is a radius of the outlet end.

2. The device as claimed in claim 1, wherein the fluid at the inlet end has an inlet pressure and the fluid at the outlet end has an outlet pressure while a difference between the inlet pressure and the outlet pressure divided by a height value of the container is the pressure gradient value.

3. The device as claimed in claim 1, wherein the flow rate value is the volume divided by the time.

4. The device as claimed in claim 1, wherein a height value of the container is larger than a radius of the inlet end and the radius of the outlet end.

5. The device as claimed in claim 1, wherein the apparatus further includes a measuring device disposed under the graduated cylinder and used for measuring weight of the volume of the fluid.

6. A method for measuring viscosity comprising the steps of:
providing a container, wherein the container is a vertical reducer having an inlet end and an outlet end, a radius of the inlet end is larger than a radius of the outlet end;
using a pressure controller connected with the inlet end and the outlet end to modulate an inlet pressure value of the fluid at the inlet end;
using the pressure controller connected with the inlet end and the outlet end to modulate an outlet pressure value of the fluid at the outlet end;
measuring a height value of the container;
modulating a pressure gradient value $dp/dz$ in accordance with the inlet pressure value, the outlet pressure value and the height value;
flowing the fluid into the container through the inlet end of the container and out of the outlet end of the container;
measuring a volume of the fluid flowing out of the outlet end and a time during the fluid flowing out of the outlet end while a flow rate value $\dot{Q}$ of the fluid flowing out of the outlet end is associated with the volume and the time; and
using a microprocessor calculating and obtaining a viscosity value $\mu$ of the fluid according to a density value $\rho$ of the fluid times acceleration, and the viscosity value $\mu$ is defined by following Expression 1:

$$\mu = \pi(\rho g + dp/dz)\gamma_{out}^4/8\dot{Q} \qquad \text{Expression 1}$$

where, g is gravity, $\gamma_{out}$ is a radius of the outlet end.

7. The method as claimed in claim 6, wherein the step of measuring a pressure gradient value of a fluid in a container includes the steps of:
measuring an inlet pressure value of the fluid at the inlet end;
measuring an outlet pressure value of the fluid at the outlet end measuring a height value of the container; and
obtaining the pressure gradient value according to the inlet pressure value, the outlet pressure value and the height value.

8. The method as claimed in claim 6, wherein the step of measuring a flow rate value of the fluid flowing out of the outlet end includes the steps of: using a graduated cylinder to measure a volume of the fluid flowing out of the outlet end; using a timer to measure a time required for the volume of the fluid to flow out of the outlet end; and obtaining the flow rate value according to the volume and the time.

9. The method as claimed in claim 6, wherein the step of measuring a flow rate value of the fluid flowing out of the outlet end includes the steps of: measuring a weight value of the fluid flowing out of the outlet end; using a timer to measure a time required for the fluid to flow out of the outlet end; and obtaining the flow rate value according to the weight value, the time and a density value of the fluid.

10. The method as claimed in claim 6, wherein in the step of obtaining a viscosity value of the fluid according to a density value of the fluid, the pressure gradient value, a radius of the outlet end, and the flow rate value, a microprocessor is used to get a viscosity value of the fluid.

* * * * *